(12) United States Patent
Chen et al.

(10) Patent No.: US 6,495,713 B2
(45) Date of Patent: Dec. 17, 2002

(54) SYNTHESIS OF KETOSULFONE ESTERS

(75) Inventors: Cheng Yi Chen, Plainsboro, NJ (US); Weirong Chen, Iselin, NJ (US); Paul O'Shea, Westmount (CA); Lushi Tan, Edison, NJ (US); Richard Tillyer, Cranford, NJ (US); Feng Xu, Staten Island, NY (US); Philippe Dagneau, Verdun (CA)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/052,088

(22) Filed: Jan. 17, 2002

(65) Prior Publication Data

US 2002/0143205 A1 Oct. 3, 2002

Related U.S. Application Data

(60) Provisional application No. 60/262,487, filed on Jan. 17, 2001, and provisional application No. 60/263,983, filed on Jan. 25, 2001.

(51) Int. Cl.[7] ................ C07C 69/66; C07C 69/34; C07C 69/52; C07C 315/00; C07C 317/00
(52) U.S. Cl. .............. 560/179; 560/187; 560/188; 560/198; 560/201; 568/31; 568/32
(58) Field of Search ................ 560/179, 187, 560/188, 198, 201; 568/31, 32

(56) References Cited

U.S. PATENT DOCUMENTS 5,883,267 A * 3/1999 Rossen et al. .............. 549/319

OTHER PUBLICATIONS

"SAR in the Alkoxy Lactone Seriers: The Discovery of DFP, a Potent and Orally Active COX–2 Inhibitor" Leblanc et al, Bioorgan & Medicinal Chemistry Letters, vol. 9, pp. 2207–2212 (1999).*

* cited by examiner

*Primary Examiner*—Mukund J. Shah
*Assistant Examiner*—Zachary C. Tucker
(74) *Attorney, Agent, or Firm*—Raynard Yuro; David L. Rose

(57) ABSTRACT

This invention encompasses a process for making a compound of Formula A

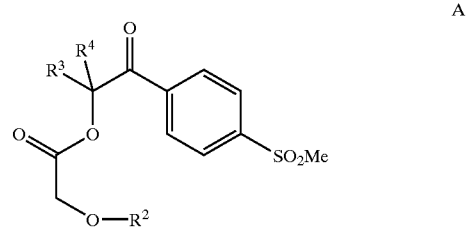

These compounds are intermediates useful in the preparation of certain non-steroidal anti-inflammnatory agents.

20 Claims, No Drawings

SYNTHESIS OF KETOSULFONE ESTERS

CROSS-REFERENCE TO RELATED APPLICATIONS

This application claims the benefit of U. S. Provisional Application No. 60/262,487, filed on Jan. 17, 2001 and Provisional Application No. 60/263,983, filed on Jan. 25, 2001.

BACKGROUND OF THE INVENTION

This invention is directed to a process for making ketosulfone esters such as (1S)-1-methyl-1-[4-(methylsulfonyl)benzoyl]propyl isopropoxyacetate. These compounds are intermediates useful in the preparation of certain non-steroidal antiinflammatory agents, such as the compounds disclosed in U.S. Pat. No. 5,981,576 and U.S. Pat. No. 6,020,343.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Up until recently, only one form of cyclooxygenase had been characterized, this corresponding to cyclooxygenase-1 or the constitutive enzyme, as originally identified in bovine seminal vesicles. Recently the gene for a second inducible form of cyclooxygenase (cyclooxygenase-2) has been cloned, sequenced and characterized from chicken, murine and human sources. This enzyme is distinct from the cyclooxygenase-1 which has now also been cloned, sequenced and characterized from sheep, murine and human sources. The second form of cyclooxygenase, cyclooxygenase-2, is rapidly and readily inducible by a number of agents including mitogens, endotoxin, hormones, cytokines and growth factors. As prostaglandins have both physiological and pathological roles, we have concluded that the constitutive enzyme, cyclooxygenase-1, is responsible, in large part, for endogenous basal release of prostaglandins and hence is important in their physiological functions such as the maintenance of gastrointestinal integrity and renal blood flow. In contrast, we have concluded that the inducible form, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

SUMMARY OF THE INVENTION

This invention encompasses a process for making a compound of Formula A

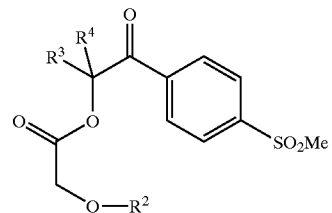

wherein $R^2$ is $C_{1-6}$alkyl, optionally substituted with $C_{3-6}$cycloalkyl, and $R^3$ and $R^4$ are $C_{1-6}$alkyl, comprising: reacting pivaloyl chloride with a compound of Formula B

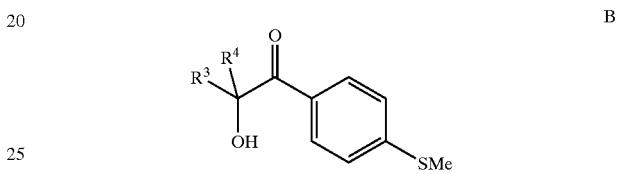

a compound of Formula C

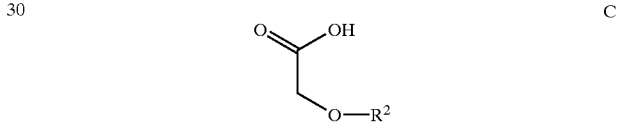

and trialkylamine in the presence of a catalyst in a substantially non-reactive solvent to yield a compound of Formula D

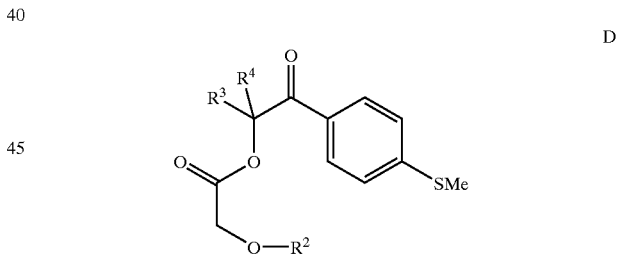

and oxidizing the compound of Formula D to yield a compound of Formula A.

These compounds are intermediates useful in the preparation of certain non-steroidal anti-inflammatory agents.

DETAILED DESCRIPTION OF THE INVENTION

U.S. Pat. No. 5,981,576, granted on Nov. 9, 1999 and U.S. Pat. No. , 6,020,343, granted on Feb. 1, 2000 are hereby incorporated by reference in their entirety.

This invention encompasses a process for making a compound of Formula A

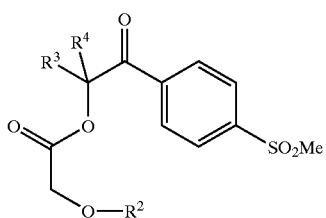

A wherein $R^2$ is $C_{1-6}$alkyl, optionally substituted with $C_{3-6}$cycloalkyl, and
$R^3$ and $R^4$ are $C_{1-6}$alkyl,
comprising: reacting pivaloyl chloride with a compound of Formula B

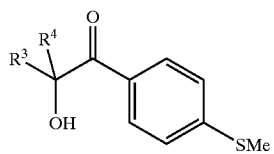

B a compound of Formula C

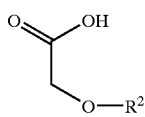

C and trialkylamine in the presence of a catalyst in a substantially non-reactive solvent to yield a compound of Formula D

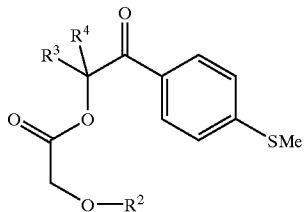

D and
oxidizing the compound of Formula D to yield a compound of Formula A.

An embodiment of the invention encompasses the process wherein trialkylamine is triethylamine.

Another embodiment of the invention encompasses the process wherein the catalyst is 4-dimethylaminopyridine.

Another embodiment of the invention encompasses the process wherein the substantially non-reactive solvent is toluene.

Another embodiment of the invention encompasses the process wherein pivaloyl chloride is sequentially the last reagent to be added.

Another embodiment of the invention encompasses the process wherein the ratio of trialkylamine to the compound of Formula B is in the range of about 2.1 to 3.1 equivalents of trialkylamine relative to about 1 equivalent of the compound of Formula B.

Another embodiment encompasses the process wherein the ratio of pivaloyl chloride to the compound of Formula B is less than about 2.5 equivalents of pivaloyl chloride relative to about 1 equivalent of the compound of Formula B. Preferably, the equivalence ratio of pivaloyl chloride to the compound of Formula B is about 1.5 to 1.

Another embodiment encompasses the process wherein the ratio of the compound of Formula C to the compound of Formula B is at least about 1.2 equivalents of the compound of Formula C relative to about 1 equivalent of the compound of Formula B and the ratio of the catalyst to the compound of Formula B is at least about 0.3 equivalents of the catalyst relative to about 1 equivalent of the compound of Formula B.

Another embodiment of the invention encompasses the process further comprising of making the compound of Formula A at ambient temperature.

Another embodiment of the invention encompasses the process wherein conversion to the compound of Formula D is greater than about 95%.

The invention also encompasses the process further comprising of making the compound of Formula B by reacting a compound of Formula E

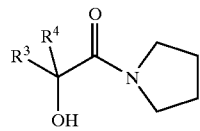

E with a lithiating agent and a compound of Formula F

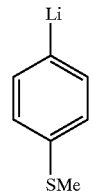

F in a substantially non-reactive solvent at a reduced temperature to produce a compound of Formula B. The term "lithiating agent" means for example n-butyllithium, hexyllithium and phenyllithium. Preferably, the reduced temperature is about −35° C. to about −30° C. Within this embodiment is encompassed this process further comprising of making the compound of Formula E by reacting a compound of Formula G

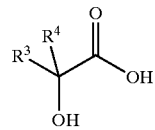

G with pyrrolidine and thionyl chloride in a substantially non-reactive solvent at a reduced temperature to produce a compound of Formula E. Preferably the reduced temperature is below about −5° C.

The invention also encompasses a process for making a compound of Formula A1

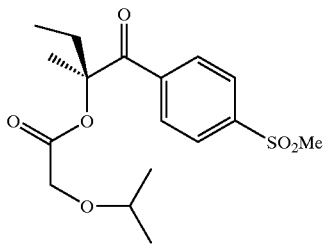

comprising: reacting pivaloyl chloride to a mixture of a compound of Formula B1

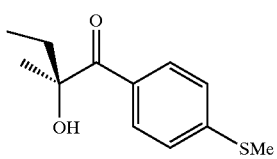

a compound of Formula C1

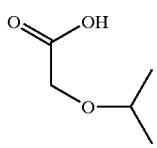

and trialkylamine in the presence of a catalyst in a substantially non-reactive solvent to yield a compound of Formula D1

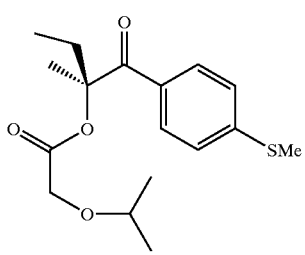

and
oxidizing the compound of Formula D1 to yield a compound of Formula A1.

Within this embodiment is encompassed the process wherein trialkylamine is triethylamine.

Within this embodiment is encompassed the process wherein the catalyst is 4-dimethylaminopyridine.

Within this embodiment is encompassed the process wherein the substantially non-reactive solvent is toluene.

Within this embodiment is encompassed the process wherein the ratio of trialkylamine to the compound of Formula B1 is in the range of about 2.1 to 3.1 equivalents of trialkylamine relative to about 1 equivalent of the compound of Formula B1.

Within this embodiment is encompassed the process wherein the ratio of pivaloyl chloride to the compound of Formula B1 is less than about 2.5 equivalents of pivaloyl chloride relative to about 1 equivalent of the compound of Formula B1. Preferably, the equivalence ratio of pivaloyl chloride to the compound of Formula B1 is about 1.5 to 1.

Within this embodiment is encompassed the process wherein the ratio of the compound of Formula C1 to the compound of Formula B1 is at least about 1.2equivalents of the compound of Formula C relative to about 1 equivalent of the compound of Formula B1 and the ratio of the catalyst to the compound of Formula B1 is at least about 0.3 equivalents of the catalyst relative to about 1 equivalent of the compound of Formula B1.

Within this process is encompassed the process wherein conversion to the compound of Formula D1 is greater than about 95%.

For the purposes of this specification, the term "alkyl" means linear or branched structures containing the indicated number of carbon atoms. Examples of alkyl groups include methyl, ethyl, propyl, isopropyl, butyl, s- and t-butyl, and the like.

"Cycloalkyl" means cyclic alkyl structures containing the indicated number of carbon atoms. Examples of cycloalkyl include cyclopropyl, cyclopentyl, cycloheptyl, and the like.

The term "trialkylamine" means tertiary alkyl substituted amines. The alkyl portions may contain 1 to 10 carbon atoms. Examples of trialkylamine include triethylamine, trimethylamine, ethyldimethylamine and the like.

The term "catalyst" means 4-dimethylaminopyridine (DMAP), pyridine or other pyridine derivatives.

The term "substantially non-reactive solvent" means, for example, toluene, benzene, xylene, etheral solvents such as diethyl ether, di-n-butyl and diisopentyl ethers, anisole, cyclic ethers such as tetrahydropyran, 4-methyl-1,3-dioxane, dihydropyran, tetrahydrofurfuryl, methyl ether, ethyl ether, 2-ethoxytetrahydrofuran and tetrahydrofuran (THF), ester solvents including ethyl and isopropyl acetate, halo carbon solvents including mono or dihalo $C_{1-4}$alkyl such as dichloromethane, and $C_{6-10}$linear, branched or cyclic hydrocarbon solvents including hexane. Mixtures of two or more of the aforesaid solvents are also contemplated.

The term "ambient temperature" means about 20° C.

The term "reduced temperature" means any temperature less than ambient temperature. Preferably, "reduced temperature" means below about 0° C.

The compounds of the present invention are intermediates useful in the preparation of certain non-steroidal antiinflammatory agents, such as the compounds disclosed in U.S. Pat. No. 5,981,576 and U.S. Pat. No. 6,020,343. For example, the compound of Formula A1

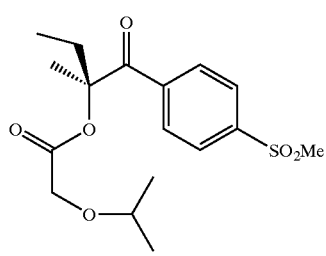

can be used in the process described herein with diazobicyclo[5.4.0]undec-7-ene (DBU) to afford the following compound

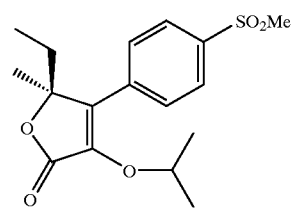

which is useful as a selective cyclooxygenase-2 inhibitor.

Throughout the instant application, the following abbreviations have the following meanings:

EDC=1-(3-dimethylaminopropyl)-3-ethylcarbodiimide
DBU=diazobicyclo[5.4.0]undec-7-ene
DMAP=4-Dimethylaminopyridine
IPAA=isopropyloxyacetic acid
Me=methyl
THF=tetrahydrofuran The invention is illustrated in connection with the following generic scheme 1

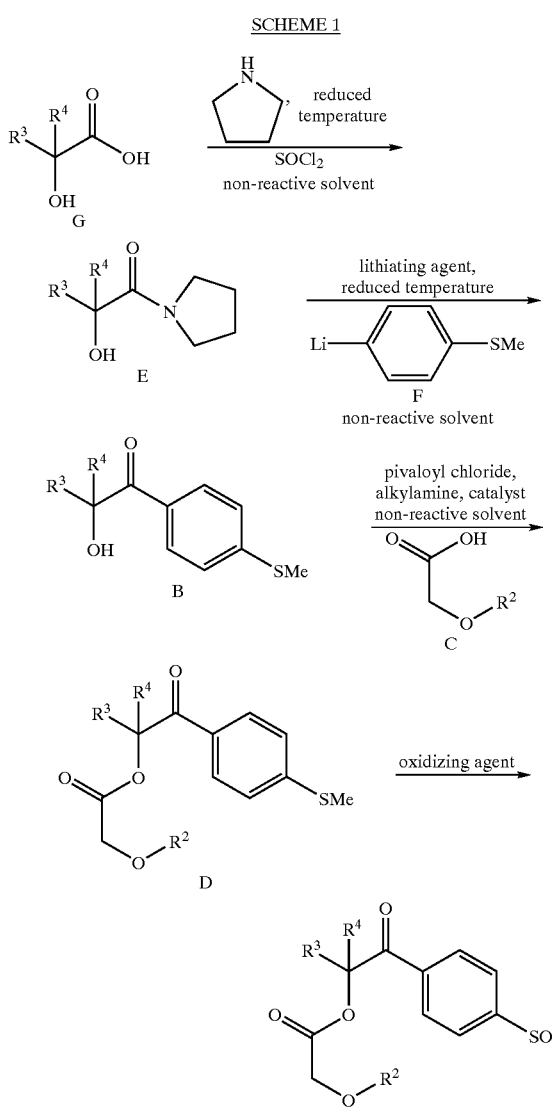

Conversion of acid G to amide E (SOCl$_2$, pyrrolidine, substantially nonreactive solvent) followed by arylation at low temperature (compound of Formula F, lithiating agent, substantially non-reactive solvent, −35 to −5° C.) provides the hydroxyketone B. Coupling of the hydroxyketone with a compound of Formula C (pivaloyl chloride, trialkylamine, catalyst, non-reactive solvent) followed by oxidation provides the ketosulfone ester A.

The invention will now be illustrated by the following non-limiting examples:

EXAMPLE 1

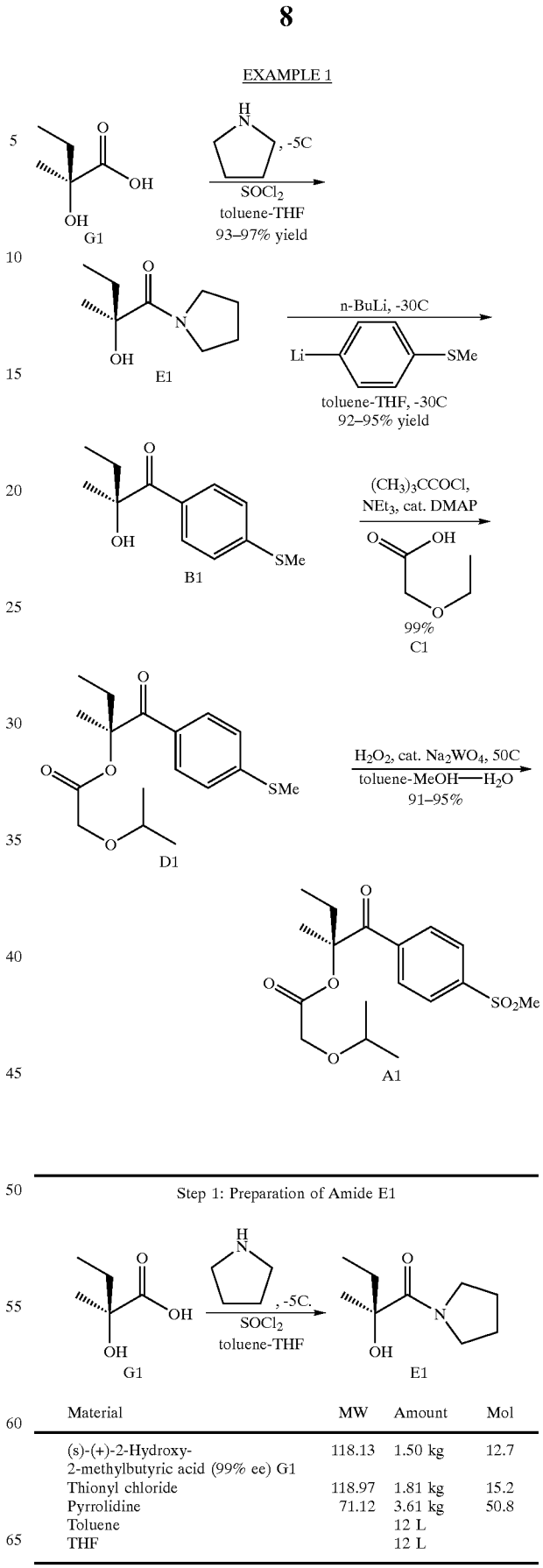

Step 1: Preparation of Amide E1

| Material | MW | Amount | Mol |
|---|---|---|---|
| (s)-(+)-2-Hydroxy-2-methylbutyric acid (99% ee) G1 | 118.13 | 1.50 kg | 12.7 |
| Thionyl chloride | 118.97 | 1.81 kg | 15.2 |
| Pyrrolidine | 71.12 | 3.61 kg | 50.8 |
| Toluene | | 12 L | |
| THF | | 12 L | |

To a mixture of 12 L of THF and 12 L of toluene cooled between −15° C. and −10° C. was added 1.11 L of neat thionyl chloride (1.81 kg; 15.2 mol; 1.2 eq.). (S)-(+)-2-Hydroxy-2-methylbutyric acid with min. 99%ee (1.5 kg, 12.7 mol, 1.0 eq.) was added portionwise as a solid to the cold mixture. Neat pyrrolidine (3.61 kg; 50.8 mol; 4.0 eq.) was added dropwise over 2.5 h, keeping the temperature below −5° C. The mixture was aged at −5° C. for 20 min or until completion of the reaction (<2% acid by HPLC).

The reaction was quenched at −10° C. to −5° C. by addition of 750 mL of saturated aqueous sodium chloride followed by 2.63 L of water. The layers were separated at room temperature. The aqueous was back extracted with 7.5 L of toluene. Organic layers were combined and subsequently washed with 4.5 L of a 3:1 (v/v) solution of brine and 2 N sodium hydroxide. The organic solution was concentrated to 50 to 70 wt % of amide in toluene, and a constant volume azeotropic distillation was conducted to dry the solution (KF <250 mg/L) to give 2.09 kg of amide E1 (96%).

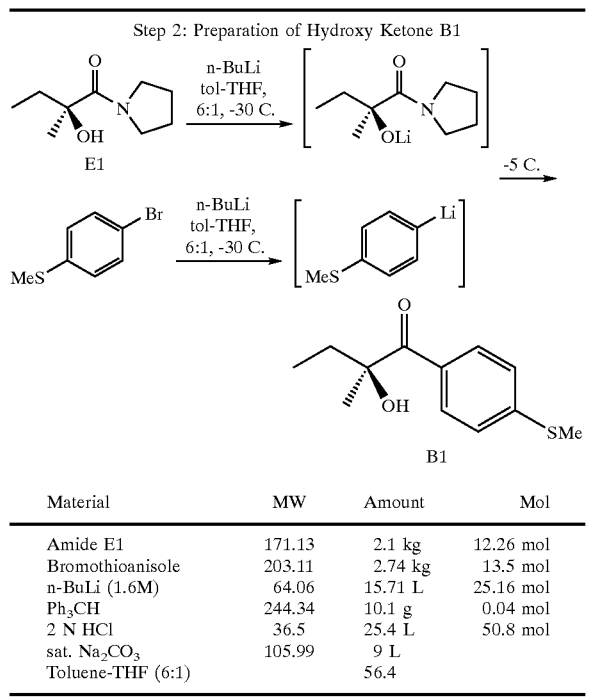

Step 2: Preparation of Hydroxy Ketone B1

| Material | MW | Amount | Mol |
|---|---|---|---|
| Amide E1 | 171.13 | 2.1 kg | 12.26 mol |
| Bromothioanisole | 203.11 | 2.74 kg | 13.5 mol |
| n-BuLi (1.6M) | 64.06 | 15.71 L | 25.16 mol |
| Ph₃CH | 244.34 | 10.1 g | 0.04 mol |
| 2 N HCl | 36.5 | 25.4 L | 50.8 mol |
| sat. Na₂CO₃ | 105.99 | 9 L | |
| Toluene-THF (6:1) | | 56.4 | |

To a 6:1 toluene:THF mixture (toluene 21.2 L, THF 4.04 L) was added a solution of amide E1 in toluene (3 L) (2.1 kg assayed amide, 12.26 mol; 1.0 eq.) and 10.1 g of triphenylmethane (41 mmol; 0.0034 eq.). The solution (KF<250 mg/L, sieve dry THF if necessary) was degassed. The mixture was cooled between −35 and −30° C. and 1.6 M n-butyllithium (7.66 L, 12.26 mol; 1.0 eq.) was added slowly over 2–4 h, keeping the temperature below −30° C.

In another flask, 4-bromothioanisole (2.74 kg, 13.5 mol; 1.15 eq.) was dissolved in 28.2 L of a 6:1 mixture of toluene-THF and cooled between −35 and −30° C. The solution was also degassed thoroughly. n-Butyllithium (1.6 M, 8.05L, 12.9 mol, 1,05 eq.) was added slowly to the cold solution over 2 h to form a white slurry, keeping the temperature below −30° C.

The amide-alkoxide solution was transferred into the lithium slurry in about 30 min via cannula and the solution was warmed to −15° C. in 1 h and to −5° C. in another hour. The mixture was aged at −5° C. until the completion of the reaction. The homogeneous mixture was cannulated into 25.4 L of ice-cold aqueous 2N hydrochloric acid with vigorous stirring. The layers were separated at room temperature and the organic layer was washed with 9 L of saturated sodium bicarbonate and concentrated to 11 L. A constant volume azeotropic distillation was conducted to remove BuBr (<0.1%A vs toluene). This affords 2.38 kg (91%) of hydroxyketone B1 (Assay purity, 82 A% excluding solvent peaks).

Step 3: Preparation of Ketoester Sulfide D1 by Pivaloyl Chloride Mediated Coupling

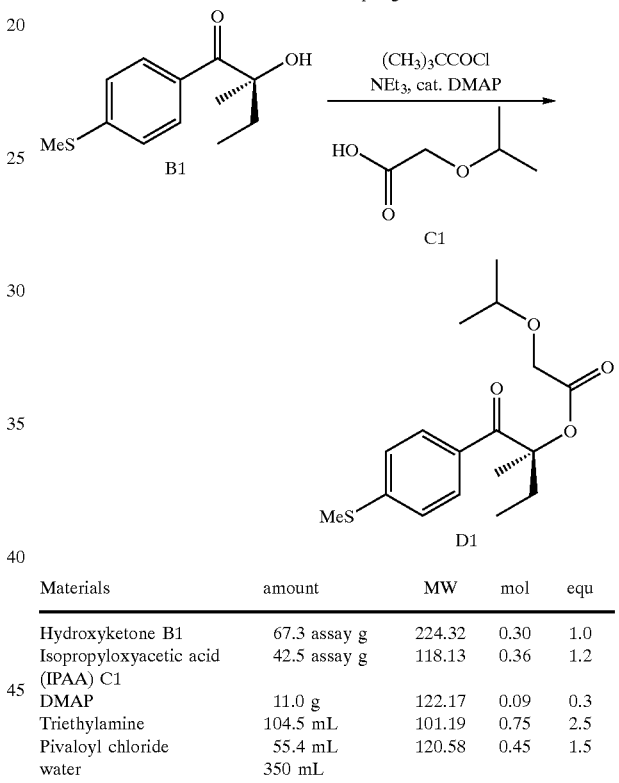

| Materials | amount | MW | mol | equ |
|---|---|---|---|---|
| Hydroxyketone B1 | 67.3 assay g | 224.32 | 0.30 | 1.0 |
| Isopropyloxyacetic acid (IPAA) C1 | 42.5 assay g | 118.13 | 0.36 | 1.2 |
| DMAP | 11.0 g | 122.17 | 0.09 | 0.3 |
| Triethylamine | 104.5 mL | 101.19 | 0.75 | 2.5 |
| Pivaloyl chloride | 55.4 mL | 120.58 | 0.45 | 1.5 |
| water | 350 mL | | | |

Under nitrogen, to a three-necked round bottom flask equipped with a mechanical stirrer, nitrogen inlet and a thermocouple was charged hydroxyketone B1 (67.3 assay g, 1.0 eq) in toluene, isopropoxyacetic acid C1 (42.5 assay g, 1.2 eq) in toluene and DMAP (11.0 g, 0.3 eq). The mixture was cooled to 10° C. and triethylamine (104.5 mL, 2.5 eq) was added followed by pivaloyl chloride (55.4 mL, 1.5 eq). The reaction mixture was then aged at room temperature for 3 to 4 h.

The reaction mixture was quenched with water (350 mL) and aged at ambient temperature for 1 h. Two layers were separated and the organic solution was used directly for the oxidation reaction.

Step 4: Preparation of Ketosulfone Ester A1

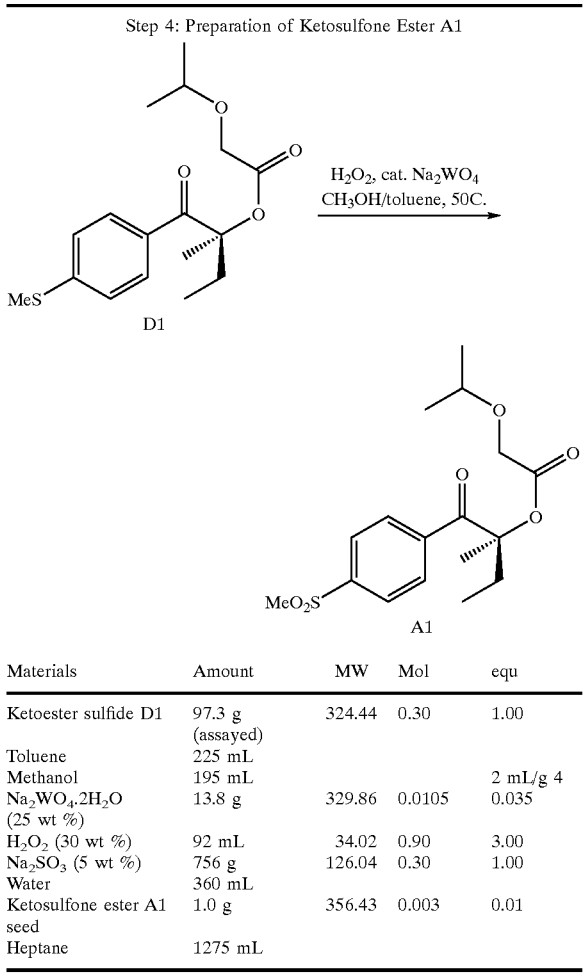

| Materials | Amount | MW | Mol | equ |
|---|---|---|---|---|
| Ketoester sulfide D1 | 97.3 g (assayed) | 324.44 | 0.30 | 1.00 |
| Toluene | 225 mL | | | |
| Methanol | 195 mL | | | 2 mL/g 4 |
| $Na_2WO_4 \cdot 2H_2O$ (25 wt %) | 13.8 g | 329.86 | 0.0105 | 0.035 |
| $H_2O_2$ (30 wt %) | 92 mL | 34.02 | 0.90 | 3.00 |
| $Na_2SO_3$ (5 wt %) | 756 g | 126.04 | 0.30 | 1.00 |
| Water | 360 mL | | | |
| Ketosulfone ester A1 seed | 1.0 g | 356.43 | 0.003 | 0.01 |
| Heptane | 1275 mL | | | |

The ketosulfone ester A1 seed can be synthesized according to the procedure shown in Example 149 of U. S. Pat. No. 6,020,343.

Under nitrogen, to a three-necked round bottom flask equipped with a mechanical stirrer, nitrogen inlet and a thermocouple was charged ketoester sulfide D1 (97.3 assay g, 1.0 eq) in toluene, toluene (225 mL), methanol (195 mL) and 25% sodium tungstate dihydrate solution (13.8, 0.35 eq) at room temperature.

The mixture was heated to 50° C. and hydrogen peroxide (9.2 mL, 10% of the total peroxide charge) was added via an addition funnel. The mixture was aged at 50° C. for 10 min and a sample was taken for HPLC assay to ensure the initiation of reaction. Once the reaction was initiated, the remaining hydrogen peroxide (82.8 ml) was charged slowly, keeping the temperature around 50° C. with sufficient cooling. The two-phased reaction mixture was aged at 50° C. for additional 3.5 h.

The reaction mixture was cooled to 10° C. and quenched with sodium sulfite (756 g, 5 wt % aq, 1.0 equiv). The layers were separated and the organic layer was washed with water (360 mL).

The organic layer was concentrated to ~362 mL (295 g/L) and heptane (121 mL) was added followed by ketosulfone ester A1 seed (1.0 g, 1%). The seeded solution was aged for 20 min and the rest of heptane (1154 mL) was charged overnight at room temperature. The resulting slurry was cooled to 0° C., aged for 30 min, and filtered. The solid was washed sequentially with cold (0° C.) 15 v/v % toluene/heptane (300 mL) then heptane (300 mL) before dried under vacuum.

Typically, the quality of the ketosulfone ester A1is 90–95 A%, >95 wt % and 99% ee.

An alternative process for making the keto sulfide D1 is illustrated below:

EXAMPLE 2
Step 3: Preparation of Ketoester Sulfide D1 by EDC Mediated Coupling

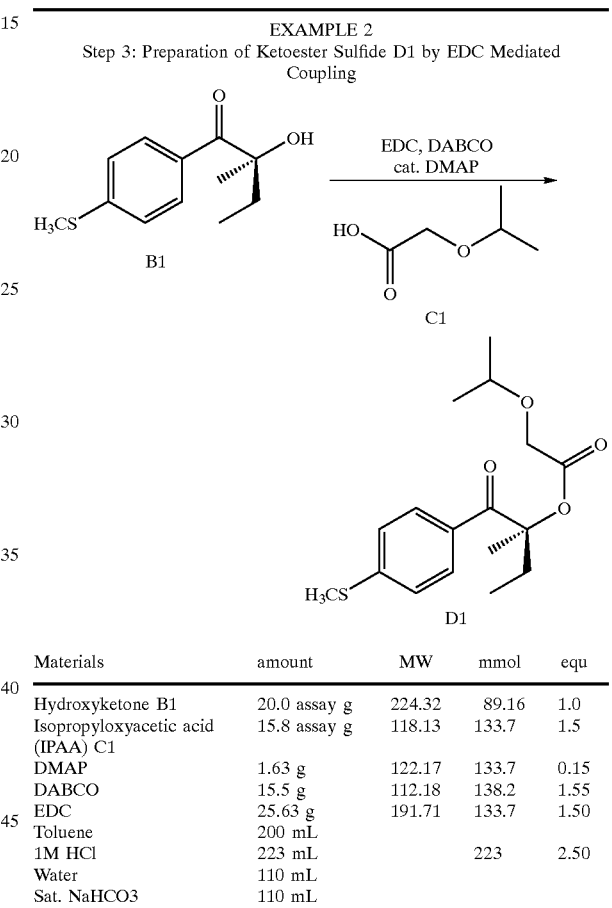

| Materials | amount | MW | mmol | equ |
|---|---|---|---|---|
| Hydroxyketone B1 | 20.0 assay g | 224.32 | 89.16 | 1.0 |
| Isopropyloxyacetic acid (IPAA) C1 | 15.8 assay g | 118.13 | 133.7 | 1.5 |
| DMAP | 1.63 g | 122.17 | 133.7 | 0.15 |
| DABCO | 15.5 g | 112.18 | 138.2 | 1.55 |
| EDC | 25.63 g | 191.71 | 133.7 | 1.50 |
| Toluene | 200 mL | | | |
| 1M HCl | 223 mL | | 223 | 2.50 |
| Water | 110 mL | | | |
| Sat. NaHCO3 | 110 mL | | | |

A solution of hydroxyketone B1 (assay 20.0 g) in toluene (180 mL) was charged sequentially with DMAP (1.63 g), DABCO (15.50 g) and EDC (25.63 g) at room temperature. The slurry was allowed to stir for 10 min and a solution of isoproproxy acetic acid C1 (15.8 g) in toluene (20 mL) was added at room temperature in one portion. The addition was slightly exothermic. After the addition, the slurry was aged at 30–35° C. with heating for 2–3 h to achieve >99% conversion by HPLC.

The reaction mixture was cooled with ice-water bath below 10° C. and 1 N HCl (223 mL) was added. Inorganic salts were dissolved to give a two-phase mixture. The organic layer was separated and washed with sat. $NaHCO_3$ (110 mL) and water (110 mL) to give ketoester sulfide D1 as a toluene solution, which was used for the oxidation step without further treatment.

What is claimed is:

1. A process for making a compound of Formula A

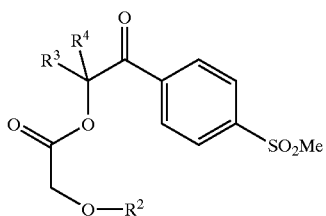

A wherein R² is C₁₋₆alkyl, optionally substituted with C₃₋₆cycloalkyl, and

R³ and R⁴ are C₁₋₆alkyl, comprising: reacting pivaloyl chloride with a compound of Formula B

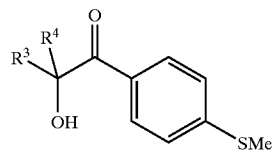

B a compound of Formula C

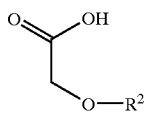

C and trialkylamine in the presence of a catalyst in a substantially non-reactive solvent to yield a compound of Formula D

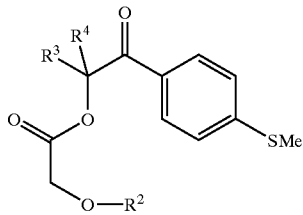

D and oxidizing the compound of Formula D to yield a compound of Formula A.

2. The process according to claim 1 wherein trialkylamine is triethylamine.

3. The process according to claim 1 wherein the catalyst is 4-dimethylaminopyridine.

4. The process according to claim 1 wherein the substantially non-reactive solvent is toluene.

5. The process according to claim 1 wherein pivaloyl chloride is sequentially the last reagent to be added.

6. The process according to claim 1 wherein the ratio of trialkylamine to the compound of Formula B is in the range of about 2.1 to 3.1 equivalents of trialkylamine relative to about 1 equivalent of the compound of Formula B.

7. The process according to claim 1 wherein the ratio of pivaloyl chloride to the compound of Formula B is less than about 2.5 equivalents of pivaloyl chloride relative to about 1 equivalent of the compound of Formula B.

8. The process according to claim 1 wherein the ratio of the compound of Formula C to the compound of Formula B is at least about 1.2 equivalents of the compound of Formula C relative to about 1 equivalent of the compound of Formula B and the ratio of the catalyst to the compound of Formula B is at least about 0.3 equivalents of the catalyst relative to about 1 equivalent of the compound of Formula B.

9. The process according to claim 1 further comprising of making the compound of Formula A at ambient temperature.

10. The process according to claim 1 wherein conversion to the compound of Formula D is greater than about 95%.

11. The process according to claim 1 further comprising making the compound of Formula B by reacting a compound of Formula E

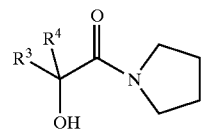

E with a lithiating agent and a compound of Formula F

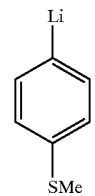

F in a substantially non-reactive solvent at a reduced temperature to produce a compound of Formula B.

12. The process according to claim 11 further comprising making the compound of Formula E by reacting a compound of Formula G

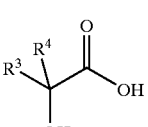

G with pyrrolidine and thionyl chloride in a substantially non-reactive solvent at a reduced temperature to produce a compound of Formula E.

13. A process for making a compound of Formula A1

A1 comprising: reacting pivaloyl chloride to a mixture of a compound of Formula B1 a compound of Formula C1

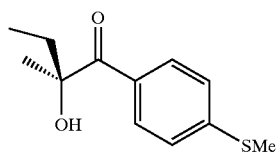

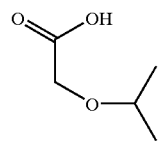

and trialkylamine in the presence of a catalyst in a substantially non-reactive solvent to yield a compound of Formula D1

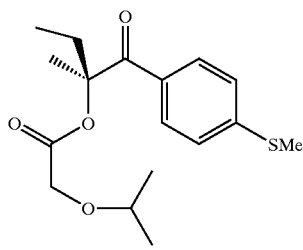

and
oxidizing the compound of Formula D1 to yield a compound of Formula A1.

14. The process according to claim 13 wherein trialkylamine is triethylamine.

15. The process according to claim 13 wherein the catalyst is 4-dimethylaminopyridine.

16. The process according to claim 13 wherein the substantially non-reactive solvent is toluene.

17. The process according to claim 13 wherein the ratio of trialkylamine to the compound of Formula B1 is in the range of about 2.1 to 3.1 equivalents of trialkylamine relative to about 1 equivalent of the compound of Formula B1.

18. The process according to claim 13 wherein the ratio of pivaloyl chloride to the compound of Formula B1 is less than about 2.5 equivalents of pivaloyl chloride relative to about 1 equivalent of the compound of Formula B1.

19. The process according to claim 13 wherein the ratio of the compound of Formula C1 to the compound of Formula B1 is at least about 1.2 equivalents of the compound of Formula C relative to about 1 equivalent of the compound of Formula B1 and the ratio of the catalyst to the compound of Formula B1 is at least about 0.3 equivalents of the catalyst relative to about 1 equivalent of the compound of Formula B1.

20. The process according to claim 13 wherein conversion to the compound of Formula D1 is greater than about 95%.

* * * * *